United States Patent [19]
Nelson

[11] Patent Number: 5,387,680
[45] Date of Patent: Feb. 7, 1995

[54] C-22 RING STABILIZED RAPAMYCIN DERIVATIVES

[75] Inventor: Frances C. Nelson, Yardley, Pa.

[73] Assignee: American Home Products Corporation, Madison, N.J.

[21] Appl. No.: 105,090

[22] Filed: Aug. 10, 1993

[51] Int. Cl.⁶ .................. C07D 491/06; A61K 31/395
[52] U.S. Cl. .................... 540/456; 540/452
[58] Field of Search ................. 540/452, 456

[56] References Cited

U.S. PATENT DOCUMENTS

| | | | |
|---|---|---|---|
| 3,929,992 | 12/1975 | Sehgal et al. | 540/456 |
| 3,993,749 | 11/1976 | Sehgal et al. | 540/456 |
| 4,316,885 | 2/1982 | Rakhit | 424/122 |

(List continued on next page.)

FOREIGN PATENT DOCUMENTS

| | | | |
|---|---|---|---|
| 507555A1 | 3/1992 | European Pat. Off. | 540/456 |
| 525960A1 | 6/1992 | European Pat. Off. | 540/456 |

OTHER PUBLICATIONS

Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L. Fifth Int. Conf. Inflamm. Res. Assoc. 121 (Abstract) (1990).

(List continued on next page.)

Primary Examiner—Robert T. Bond
Attorney, Agent, or Firm—Steven R. Eck

[57] ABSTRACT

This invention provides C-22 substituted rapamycin derivatives of the following formulas:

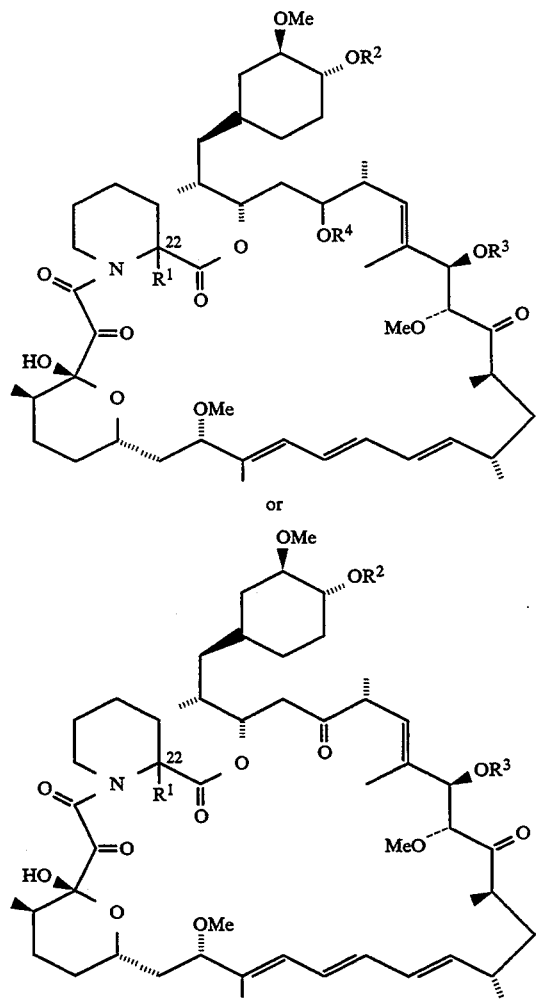

and pharmaceutically acceptable salts thereof which are useful for inducing immunosuppression and treating transplantation rejection, host vs. graft disease, autoimmune diseases, diseases of inflammation, solid tumors, fungal infections, adult T-cell leukemia/lymphomas and hyperproliferative vascular disorders.

7 Claims, No Drawings

U.S. PATENT DOCUMENTS

| | | | |
|---|---|---|---|
| 4,401,653 | 8/1983 | Eng | 540/456 |
| 4,650,803 | 3/1987 | Stella et al. | 514/291 |
| 4,885,171 | 12/1989 | Surendra et al. | 540/456 |
| 5,078,999 | 1/1992 | Warner et al. | 424/122 |
| 5,080,899 | 1/1992 | Sturm et al. | 424/122 |
| 5,091,389 | 2/1992 | Ondeyka et al. | 514/291 |
| 5,100,883 | 3/1992 | Schiehser | 514/183 |
| 5,100,899 | 3/1992 | Calne | 514/291 |
| 5,102,876 | 4/1992 | Caufield et al. | 514/183 |
| 5,118,677 | 6/1992 | Caufield | 514/183 |
| 5,118,678 | 6/1992 | Kao et al. | 514/183 |
| 5,120,842 | 6/1992 | Failli et al. | 540/452 |
| 5,130,307 | 7/1992 | Failli et al. | 540/452 |
| 5,138,051 | 8/1992 | Hughes et al. | 540/456 |
| 5,151,413 | 9/1992 | Caufield et al. | 514/63 |
| 5,162,333 | 11/1992 | Failli et al. | 514/291 |
| 5,169,851 | 12/1992 | Hughes et al. | 514/291 |
| 5,177,203 | 1/1993 | Failli et al. | 514/291 |
| 5,194,447 | 3/1993 | Kao | 514/542 |

OTHER PUBLICATIONS

Meiser, B. M., J. Heart Lung Transplant 11 (pt 2): 197 (1992).

Meiser, B. M., J. Heart Lung Transplant 9: 55 (1990).

Stepkowski, S. M., Transplantation Proceedings 23(1): 507–508 (1991).

C-22 RING STABILIZED RAPAMYCIN DERIVATIVES

BACKGROUND OF THE INVENTION

This invention relates to C-22 ring stabilized rapamycin derivatives, or pharmaceutically acceptable salts thereof, which are useful for inducing immunosuppression, and for treating transplantation rejection, host vs. graft disease, autoimmune diseases, diseases of inflammation, solid tumors, fungal infections, adult T-cell leukemia/lymphomas and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions. U.S. Pat. No. 5,118,678 discloses carbamates of rapamycin that are useful as immunosuppressive, antiinflammatory, antifungal, and antitumor agents. U.S. Pat. No. 5,100,883 discloses fluorinated esters of rapamycin. U.S. Pat. No. 5,118,677 discloses amide esters of rapamycin. U.S. Pat. No. 5,130,307 discloses aminoesters of rapamycin. U.S. Pat. No. 5,117,203 discloses sulfonates and sulfamates of rapamycin. U.S. Pat. No. 5,194,447 discloses sulfonylcarbamates of rapamycin.

DESCRIPTION OF THE INVENTION

This invention concerns C-22 substituted rapamycin derivatives which possess immunosuppressive and/or antifungal and/or antiinflammatory activity in vivo and/or inhibit thymocyte proliferation in vitro. These compounds are, therefore, useful in the treatment of *Candida albicans* infections, diseases of inflammation and transplant rejection autoimmune diseases, including lupus, rheumatoid arthritis, diabetes mellitus, multiple sclerosis, etc.

More particularly, the present invention concerns rapamycin derivatives that are stabilized by substitution at the C-22 position, and all pharmaceutically acceptable salts thereof. Such derivatives have the structure:

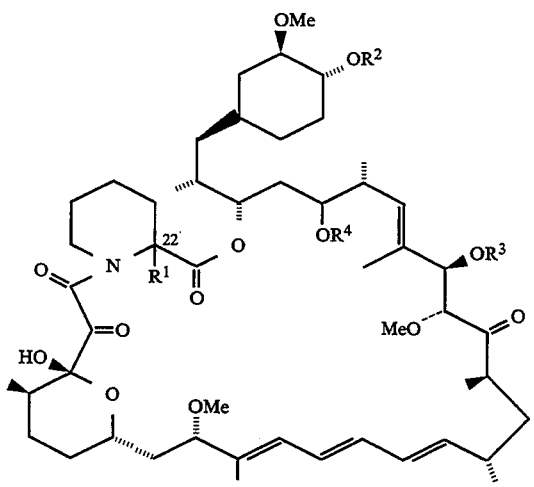

or

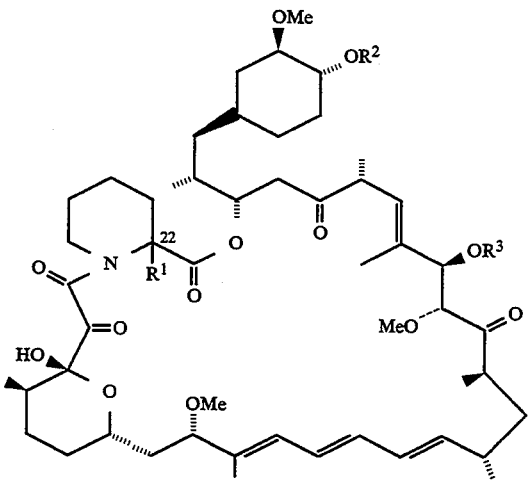

wherein
$R^1$ is $C_1$–$C_6$ lower alkyl, $C_1$–$C_6$ lower acyl, $C_1$–$C_6$ alkylthio, aryl, arylalkyl, arylthio, arylalkylthio, cyano, or $C_1$–$C_6$ perfluorinated lower alkyl; and
$R^2$, $R^3$, and $R^4$ are each independently:
 a.) hydrogen; or
 b.) $SiEt_3$; or c.) 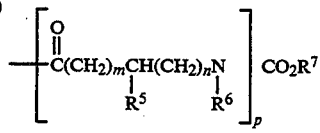

wherein

R⁵ is hydrogen, alkyl of 1-6 carbon atoms, aminoalkyl of 1-4 carbon atoms, aralkyl of 7-10 carbon atoms, —(CH₂)$_q$CO₂R⁸, —(CH₂)$_r$NR⁹CO₂R¹⁰, carbamylalkyl of 2-3 carbon atoms, hydroxyalkyl of 1-4 carbon atoms, guanylalkyl of 2-4 carbon atoms, mercaptoalkyl of 1-4 carbon atoms, alkylthioalkyl of 2-6 carbon atoms, indolylmethyl, hydroxyphenylmethyl, imidazoylmethyl or phenyl which is optionally mono-, di- or tri-substituted with a substituent selected form alkyl of 1-6 carbon atoms, alkoxy of 1-6 carbon atoms, hydroxy, cyano, halo, nitro, carbalkoxy of 2-7 carbon atoms, trifluoromethyl, amino, or a carboxylic acid.

R⁶ and R⁹ are each, independently, hydrogen, alkyl of 1-6 carbon atoms, or aralkyl of 7-10 carbon atoms.

R⁷, R⁸, and R¹⁰ are each, independently, alkyl of 1-6 carbon atoms, aralkyl of 7-10 carbon atoms, fluorenylmethyl, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or a carboxylic acid;

m is 0-4;
n is 0-4;
p is 1-2;
q is 0-4;
r is 0-4; wherein
R⁵, R⁶, m, and n are independent in each of the

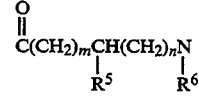

subunits when p=2; or d.) —CONH(CR¹¹R¹²)$_n$—X wherein

R¹¹ and R¹² are each, independently, hydrogen, alkyl of 1-6 carbon atoms, aralkyl of 7-10 carbon atoms, cycloalkyl of 3-8 carbon atoms, halogen, or trifluoromethyl;

X is hydrogen, lower alkyl of 1-6 carbon atoms, cycloalkyl of 3-8 carbon atoms, trifluoromethyl, nitro, alkoxy of 1-6 carbon atoms, carboalkoxy of 2-7 carbon atoms, aralkyl of 7-10 carbon atoms, halo, dialkylamino of 1-6 carbon atoms per alkyl group, thioalkyl of 1-6 carbon atoms, or Y;

Y is a phenyl group which may be optionally mono-, di-, or tri-substituted with a group selected from alkyl of 1-6 carbon atoms, aralkyl of 7-10 carbon atoms, alkoxy of 1-6 carbon atoms, cyano, halo, nitro, carbalkoxy of 2-7 carbon atoms, trifluoromethyl, dialkylamino of 1-6 carbon atoms per alkyl group, alkylthio of 1-6 carbon atoms, SO₃H, PO₃H, or CO₂H;

n=0-5;

with the proviso that R², R³ and R⁴ are not all hydrogen and when n=0, X is lower alkyl of 1-6 carbon atoms, cycloalkyl of 3-8 carbon atoms, aralkyl of 7-10 carbon atoms, or Y; or e.) 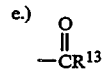

wherein

R¹³ is a mono-, di-, poly-, or per-fluorinated alkyl group of 1-10 carbon atoms, with the proviso that R², R³ and R⁴ are not all hydrogen, alkyl of 1-10 carbon atoms, arylalkyl of 7-10 carbon atoms, or aryl wherein the aryl group may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO₃H, —PO₃H, and CO₂H; or f.) 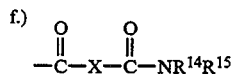

wherein

X is —(CH₂)m— or —Ar—;

R¹⁴ and R¹⁵ are each, independently, hydrogen, alkyl of 1-12 carbon atoms, —(CH2)n—Ar, —(CH₂)$_p$—NR¹⁶R¹⁷, or —(CH₂)$_p$—N+R¹⁶R¹⁷R¹⁸Y—;

R¹⁶ and R¹⁷ are each, independently, hydrogen, alkyl of 1-12 carbon atoms, or —(CH₂)$_n$—Ar;

Ar is an optionally mono- or di-substituted group selected from

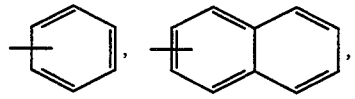

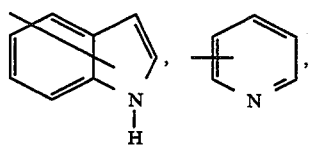

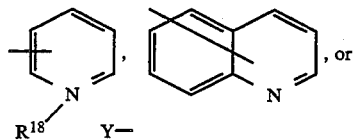

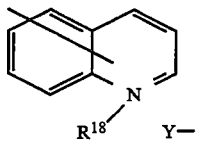

in which the optional substituents are selected from the group consisting of alkyl of 1-6 carbon atoms, aralkyl of 7-10 carbon atoms, alkoxy of 1-6 carbon atoms, cyano, halo, nitro, carbalkoxy of 2-7 carbon atoms, or perfluoroalkyl of 1-6 carbon atoms;

R⁸ is alkyl of 1-6 carbon atoms;

Y is a halide, sulfate, phosphate, or p-toluenesulfonate anion;

m=1-6;
n=1-6;
p=1-6; or g.) —CONHSO₂—Ar wherein

Ar is phenyl, naphthyl, pyridyl, quinolyl, isoquinolyl, quinoxalyl, thienyl, thionaphthyl, furyl, benzofuryl, benzodioxyl, benxoxazolyl, benzoisoxazolyl, or benzodioxolyl; wherein the Ar group may be optionally mono-, di-, or tri-substituted with a group selected from alkyl of 1-6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO$_3$H, —PO$_3$H, or CO$_2$H;

with the proviso that R$^2$, R$^3$ and R$^4$ are not all hydrogen; or a pharmaceutically acceptable salt thereof when the Ar group contains a basic nitrogen or when the Ar group is substituted by dialkylamino of 1–6 carbon atoms per alkyl group, —SO$_3$H, —PO$_3$H, or CO$_2$H.

h) —SO$_2$R$^{19}$ wherein

R$^{19}$ is alkyl, alkenyl, or alkynyl containing 1 to 6 carbon atoms; or an aromatic moiety selected from the group consisting of phenyl and naphthyl or a heterocyclic moiety selected from the group consisting of thiophenyl and quinolinyl or NHCO$_2$R$^{20}$ wherein R$^{20}$ is lower alkyl containing 1 to 6 carbon atoms; or i) 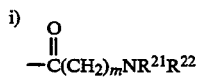

wherein

R$^{21}$ and R$^{22}$ are each hydrogen or alkyl of 1–3 carbon atoms or R$^{21}$ and R$^{22}$ together with the nitrogen to which they are attached form a saturated heterocyclic ring having 4–5 carbon atoms; and m=1–3: or j) 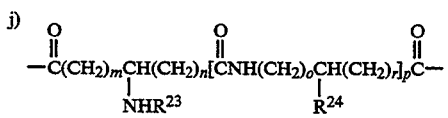

wherein

R$^{24}$ is hydrogen, alkyl of 1–6 carbon atoms, arylalkyl of 7–10 carbon atoms, (CH$_2$)$_s$NR$^{25}$R$^{26}$, aminoalkyl of 1–4 carbon atoms, hydroxyalkyl of 1–4 carbon atoms, guanylalkyl of 2–4 carbon atoms, mercaptoalkyl of 1–4 carbon atoms, alkylthioalkyl of 2–6 carbon atoms, indolmethyl, hydroxyphenylmethyl, imidazolylmethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or a carboxylic acid;

R$^{25}$ is hydrogen, alkyl of 1–6 carbon atoms, or aralkyl of 7–10 carbon atoms;

R$^{23}$ and R$^{26}$ are each independently hydrogen, formyl, alkanoyl of 2–7 carbon atoms, arylalkanoyl of 8–11 carbon atoms, aryloyl, or CO$_2$R$^{27}$;

R$^{27}$ is alkyl of 1–6 carbon atoms, arylalkyl of 7–10 carbon atoms, allyl, fluorenylmethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino or a carboxylic acid;

m is 0–4;
n is 0–4;
p is 0–1;
q is 0–4;
r is 0–4; and
s is 0–4 or a pharmaceutically acceptable salt thereof.

Of the substituents listed above as R$^1$, the more preferred are the C$_1$–C$_6$ lower alkyl groups. Of these, the most preferred are methyl and ethyl substituents. It will be understood by those skilled in the art that the R$^1$ substituents listed above may be linear or branched and may include those having additional substitution. Substituents on these R$^1$ groups may include, but are not limited to, alcohol, ketone, cyano, and halo groups. In the case of the aminoesters described in section c), above, the preferred compounds are those in which m=0, n=0, and p=1; m=0, n=0, and p=2; n=0, and R$^5$ is —(CH$_2$)$_q$CO$_2$R$^7$; m=0, n=0, and R$^5$ is —(CH$_2$)$_r$NR$^9$CO$_2$R$^{10}$; and m=0, n=0, and R$^5$ is hydrogen. Of the C$_1$–C$_6$ perfluorinated lower alkyl compounds referred to as R$^1$, the most preferred are the trifluoromethyl and trifluoroethyl substituents.

For the purposes of this disclosure, "lower alkyl", when used alone or in combination, refers to moieties having 1–6 carbon atoms in the carbon chain. The term "acyl" refers to substituents of the general structure

wherein R refers to a chain of 1–5 carbon atoms. The term "aryl", when used alone or in combination, refers to univalent aromatic substituents of 6–10 carbon atoms which have the free valence at a ring atom. Examples of these aryl groups include the phenyl, tolyl, and xylyl substituents. The term "arylalkyl" refers to aromatic substituents having between about 7 and about 16 carbon atoms, with the single valence being located in a side chain. Examples of such arylalkyl substituents include the benzyl, tolyl, benzethyl, phenethyl, and styryl groups. The terms "alkylthio", "arylthio", and "arylalkylthio" refer to substituents having the structure —SR, wherein R refers, respectively, to the "lower alkyl", "aryl", and "arylalkyl" groups just mentioned. The term "halo" refers to fluoro, chloro, bromo, or iodo.

The pharmaceutically acceptable salts of these aminoesters may be formed from inorganic cations such as sodium, potassium, and the like and organic acids such as acetic, lactic, citric, tartaric, succinic, maleic, malonic, gluconic, and the like, when R$^5$ contains a basic amino group.

Such aminoesters can be prepared by acylating rapamycin with an acylating agent having the general structure:

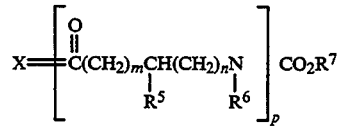

where X is OH in the presence of a coupling reagent, such as dicyclohexylcarbodiimide. The aminoesters also can be prepared using a mixed anhydride of the above described carboxylic acid as the acylating species. Alternatively, the acylating species can be an acid halide, where X can be Cl, Br or I. The acylating groups used to prepare the compounds of this invention are commercially available or can be prepared by methods that are disclosed in the literature.

Of the carbamylated compounds disclosed in section d) above, the preferred members are those in which $R^3$ is hydrogen; those in which $R^2$ is hydrogen; those in which $R^4$ is hydrogen; those in which n is 0 and X is Y; those in which $R^3$ is hydrogen, n is 0, and X is Y; and those in which n is 0, X is Y, and Y is phenyl, 4-fluorophenyl, 2,4-difluorophenyl, 4-nitrophenyl or 4-methylphenyl.

As one example of these compounds, the 31-carbamylated compounds of this invention can be prepared by protecting the 42-alcohol of rapamycin with a protecting group, such as with a tert-butyl dimethylsilyl group, followed by carbamylation of the 31-position with an isocyanate with the general structure shown above. Removal of the protective group provides the 31-carbamylated compounds. In the case of the tert-butyl dimethylsilyl protecting group, deprotection can be accomplished under mildly acidic conditions.

Having the 31-position carbamylated and the 42-position deprotected, the 42-position can be reacted with a different isocyanate than was reacted with the 31-alcohol, to give compounds having different carbamates at the 31- and 42-positions. Alternatively, the 42-carbamylated compounds, prepared as described above, can be reacted with a different isocyanate to provide compounds having different carbamates at the 31- and 42-positions.

The isocyanates used to prepare these carbamylated compounds are commercially available or can be prepared by published methods.

The pharmaceutically acceptable salts of these carbamylated rapamycin compounds are those derived form such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The preferred fluorinated esters of the group described in section e), above, are those in which $R^3$ is hydrogen; those in which $R^{13}$ is a mono-, di-, poly-, or per-fluorinated alkyl group of 1-6 carbon atoms; and those in which $R^3$ is hydrogen and $R^{13}$ is a mono-, di-, poly-, or per-fluorinated alkyl group of 1-6 carbon atoms.

When the other acylated compounds of sections c)–j) contain an aryl or arylalkyl moiety, it is preferred that the aryl portion is a phenyl, naphthyl, pyridyl, quinolyl, isoquinolyl, quinoxalyl, thienyl, thionaphthyl, furyl, benzofuryl, benzodioxyl, benzoxozolyl, benzoisoxazolyl, or benzodioxolyl group that may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO$_3$H, —PO$_3$H, and —CO$_2$H. It is more preferred that the aryl moiety is a phenyl group that is optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO$_3$H, —PO$_3$H, and —CO$_2$H.

The acylated compounds of this invention can be prepared by acylating rapamycin with an acylating agent having the general structure

where X is OH, in the presence of a coupling reagent, such as CMC (1-cyclohexyl-3-(2-morpholinoethyl) carbodiimide metho-para-toluenesulphonate). The compounds of this invention also can be prepared by using an anhydride of the above described carboxylic acid as the acylating species. In addition, the acylating species can be an acid halide, where X can be Cl, Br, or I. Alternatively, reagents such as Ishikawa's Reagent (N,N-diethyl-1,1-2,3,3,3-hexafluoropropylamine) can be used as an acylating reagent to give compounds of this invention.

The compounds of this invention acylated at each of the 27-, 31- and 42-positions can be prepared by the methods described above by increasing variables such as reaction time, temperature, and quantity of acylating agent.

As an example, the 31-acylated compounds of this invention can be prepared by protecting the 27- and 42-alcohol of rapamycin with protecting groups, such as with a tert-butyl dimethylsilyl group in the presence of a base, such as imidazole, followed by acylation of the 31-position with an acylating agent having the general structure shown above. Removal of the protecting groups provides the 31-acylated compounds. In the case of the tert-butyl dimethylsilyl protecting group, deprotection can be accomplished under mildly acidic conditions, such as with a mixture of aqueous acetic acid and THF.

Having the 31-position acylated and the 42-position deprotected, the 42-position can be reacted with a desired acylating agent to give compounds having different acyl moieties at the 31- and 42-positions. Similarly, the 42-acyl compounds, prepared as described above, can be reacted with an acylating agent having a different structure to place a different acyl group on the 31-position. The acylating groups used to prepare the compounds of the invention are commercially available or can be prepared by methods that are disclosed in the literature.

The preferred amide esters of rapamycin of those disclosed in section f), above, are those in which X is —(CH$_2$)$_m$—; those in which X is —(CH$_2$)$_m$ and $R^{14}$ and $R^{15}$ are alkyl of 1-6 carbon atoms; and those in which X is —(CH$_2$)$_m$—, $R^{14}$ is hydrogen and $R^{15}$ is Ar is —(CH$_2$)$_n$—Ar.

Pharmaceutically acceptable salts of these compounds may be formed when $R^{14}$ or $R^{15}$ is —(CH$_2$)$_p$—NR$^{15}$R$^{16}$ or when Ar is an optionally mono- or di-substituted pyridal or quinolyl group. The pharmaceutically acceptable salts are derived form such organic and inorganic acids as acetic, lactic, citric, tartaric, succinic, maleic, malonic, gluconic, hydrochloric, hydrobromic, phosphoric, nitric, sulfuric, methanesulfonic, and the like.

Production of amide esters of rapamycin is taught in U.S. Pat. No. 5,118,677, which is incorporated herein by reference.

The pharmaceutically acceptable salts of the sulfonylcarbamate rapamycin compounds described in section g), above, are those derived from such inorganic cations such as sodium, potassium, and the like; organic bases such as: mono-, di-, and trialkyl amines of 1-6 carbon atoms per alkyl group, and mono-, di-, and trihydroxyalkyl amines of 1–6 carbon atoms per alkyl group, and the like; and organic and inorganic acids such as: acetic, lactic, citric, tartaric, succinic, maleic, malonic, gluconic, hydrochloric, hydrobromic, phosphoric, nitric, sulfuric, methanesulonic, and similarly known acceptable acids.

Of these compounds, preferred members are those in which Ar is optionally mono-, di-, or tri-substituted phenyl. When Ar is substituted with arylalkyl of 7–10 carbon atoms, it is preferred that aryl portion of the arylalkyl moiety be a phenyl group.

The compounds of this invention carbamylated at one of the 27-, 31-, or 42-alcohol position or at all of the positions can be prepared by reacting rapamycin with an isocyanate having the general structure

O=C=N—SO$_2$—Ar under neutral conditions or in the presence of a base, such as pyridine.

The carbamylated compounds of this invention can be prepared by protecting the alcohol groups which are not to be reacted with a protecting group, such as with a tert-butyl dimethylsilyl group, followed by carbamylation of the unprotected position with an isocyanate having the general structure shown above. Removal of the protecting group provides the desired carbamylated compounds. In the case of the tert-butyl dimethylsilyl protecting group, deprotection can be accomplished under mildly acidic conditions.

Having one or two positions carbamylated and another position deprotected, the now unprotected position can be reacted with a different isocyanate than was reacted with the first alcohol, to give compounds having different carbamates at the positions in question The isocyanates used to prepare the compounds of the invention are commercially available or can be prepared by methods that are disclosed in the literature. March [Advanced Organic Chemistry, 3d ed., pp. 391, 452, and 479 (1985)] describes a general method for preparing arylsulfonyl isocyanates that can be used where the arylsulfonylisocyanate is not commercially available. The following scheme is illustrative of one method starting from an aryl moiety. Other methods of preparing arylsulfonyl isocyanates are known in the literature.

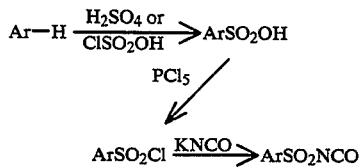

The rapamycin 27-, 31- and 42-sulfonates of this invention, as seen in section h), above, can be prepared by a standard literature procedure, as outlined by the general reaction formula below:

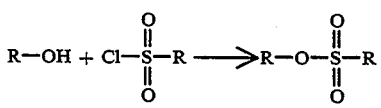

The sulfonate formation between alcohol and sulfonyl halide has been described [Jerry March, Advanced Organic Chemistry, 3rd edition, published in 1985, page 444]. The specific reaction condition employed in this invention was developed by S. Rakhit of Ayerst Laboratories and reported in U.S. Pat. No. 4,316,885 (Feb. 23, 1982).

The 27-, 31- and 42-(N-carboalkoxy)sulfamates of the present invention can also be prepared by reaction of rapamycin with an alkyl(carboxysulfamoyl)triethylammonium hydroxide inner salt (Burgess Salts; see G. M. Atkins Jr. and E. M. Burgess, J. A.m. Chem. Soc., 90, 4744, 1968; E. M. Burgess, H. R. Penton Jr. and E. A. Taylor, J. Org. Chem. 38, 26, 1978).

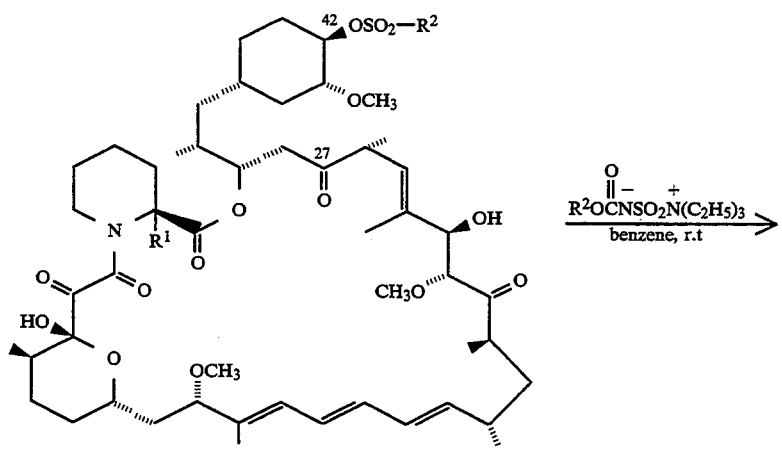

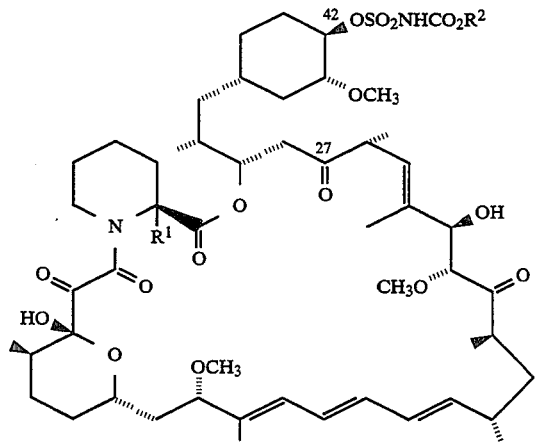

wherein $R^1$ and $R^2$ are as defined above.

The amino alkyl ester compounds of section i), above, can be prepared by acylating the desired position(s) with a suitable acylating agent as described in U.S. Pat. No. 4,650,803, the disclosure of which is incorporated herein by reference, while the remainder of the 27-, 31-, or 42-positions are protected, such as by a triethylsilyl group.

The aminodiester containing compounds of this invention, as seen in section i), above, can be prepared by acylating rapamycin with an acylating agent having the general structure:

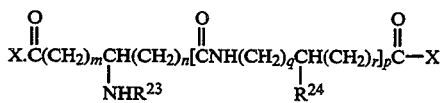

wherein $R^{23}$, $R^{24}$, m, n, p, q, and r are as defined above, and X is OH, in the presence of a coupling agent, such as dicyclohexylcarbodiimide, or a water soluble carbodiimide. The compounds of this invention also can be prepared using a mixed anhydride, or an activated ester of the above described carboxylic acid (such as those with p-nitrophenol, pentachloro or pentafluorophenol, 2,4,5-trichlorophenol, N-hydroxysuccinimide, N-hydroxypthalimide or 1-hydroxy-1H-benzotriazole) as the acylating species. Alternatively, the acylating species can be an acid halide, where X can be Cl, Br or F (except when $R^{23}$ or $R^{27}$=t-Bu), an azide or an imidazolide derivative of said acid.

The acylating groups used to prepare the compounds of this invention are commercially available or can be prepared by methods that are disclosed in the literature. The amino acids used to prepare the compounds of this invention can have either the R or S configuration, and the optically active carbon will retain its relative configuration when transformed into a compound of this invention. Where p is 1 the acylating species can typically be prepared by condensing two amino acids to form a dipeptide which is transformed into the acylating species illustrated above by standard chemical methodology.

Of these aminodiester compounds, the preferred members are those in which p is 0; and those in which p is 0, and n is 1–2. One of the more preferred aminodiesters of the present invention is C-22-methyl-42-dimethylglycine rapamycin. Synthesis data for this compound is provided below as Example 7.

It will be understood by one skilled in the art that the C-22 substituted rapamycin derivatives of this invention may include those in which each of $R^2$, $R^3$ and $R^4$ are hydrogen or in which one or two of $R^2$, $R^3$ and $R^4$ are hydrogen and the other(s) is/are a group listed above in sections b)–j). The present invention also includes those compounds of C-22 substituted rapamycin in which each of $R^2$, $R^3$, and $R^4$ are a group chosen from sections a)–j), above, including derivatives in which $R^2$, $R^3$, $R^4$ are not chosen from the same sections presented as b)–j), above. It will also be understood that the present invention includes all pharmaceutically acceptable salts, analogs, racemates and individual enantiomers of such compounds.

The C-22 substituted compounds of this invention can be prepared by first protecting the 31- and 42-hydroxyl sites and then completing substitution at the C-22 position. An example of such substitution is demonstrated by the C-22 methylation of Scheme 1, below:

Scheme 1
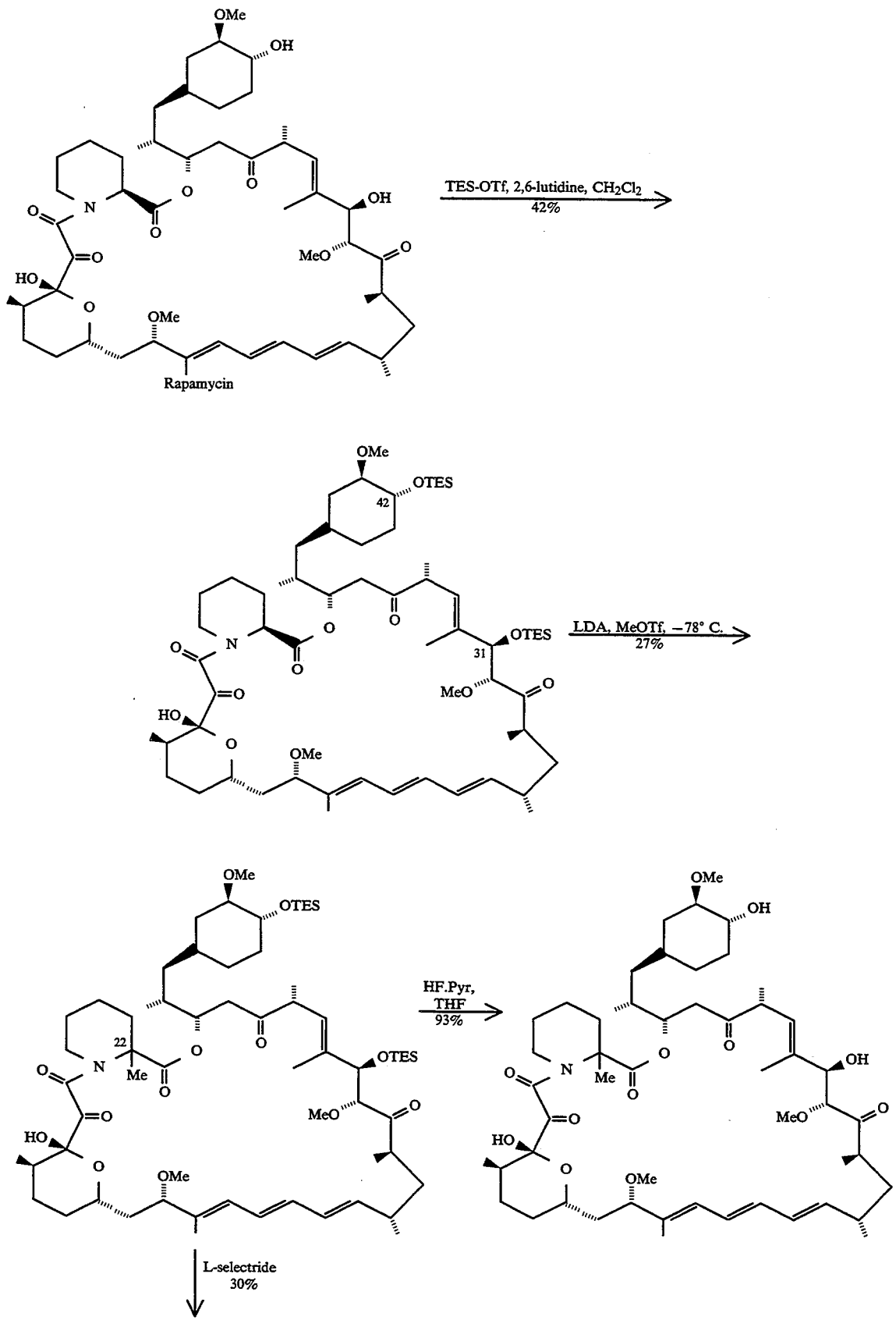

-continued
Scheme 1

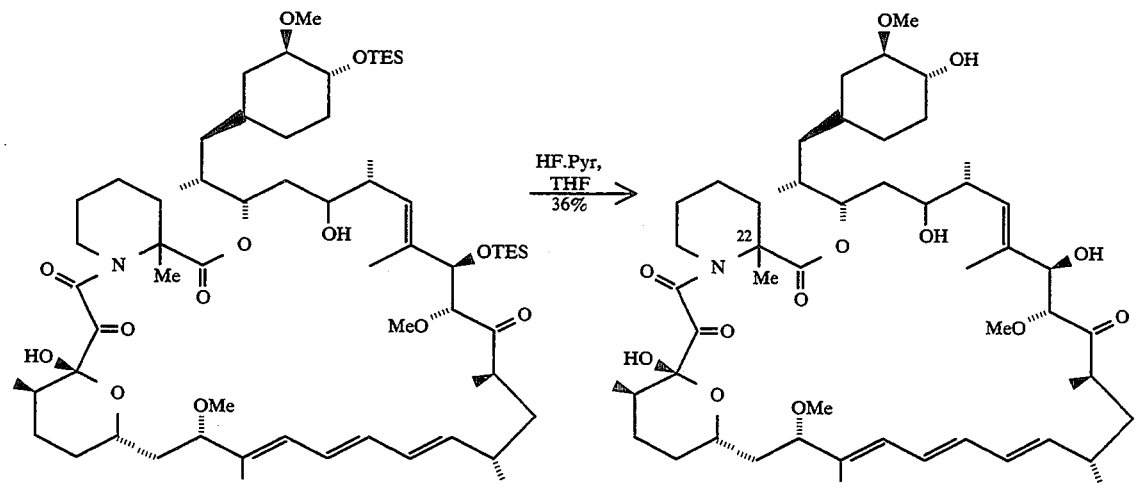

In scheme 1, which illustrates synthesis of the α-methyl compounds, the position 31- and 42-hydroxyl groups are first protected with a suitable protecting group, such as the triethylsilyl (TES) protecting group. Then the bis-TES rapamycin is treated with lithium diisopropyl amide (LDA), followed by alkylation with methyl trifluoromethanesulfonate (MeOTf). Following this scheme, alkylation occurs exclusively at the C-22 position. The TES protecting groups may then be removed via treatment with HF.Pyr complex. The 31- and 42-hydroxyl sites may then be substituted as described above. Alternatively, the C-22 substituted, TES-protected material may be reduced with L-selectride to give the C-27-hydroxy-C-22-methyl protected derivative. The 31 and 42 positions can be further functionalized as described earlier.

Other alkylations can be prepared in an analogous manner. Scheme 2, below, illustrates the C-22 ethylation of rapamycin.

Scheme 2

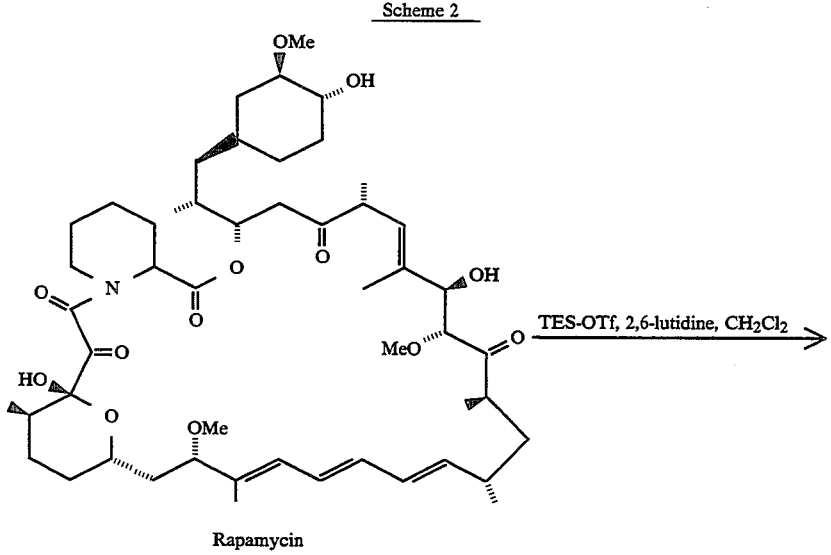

Rapamycin

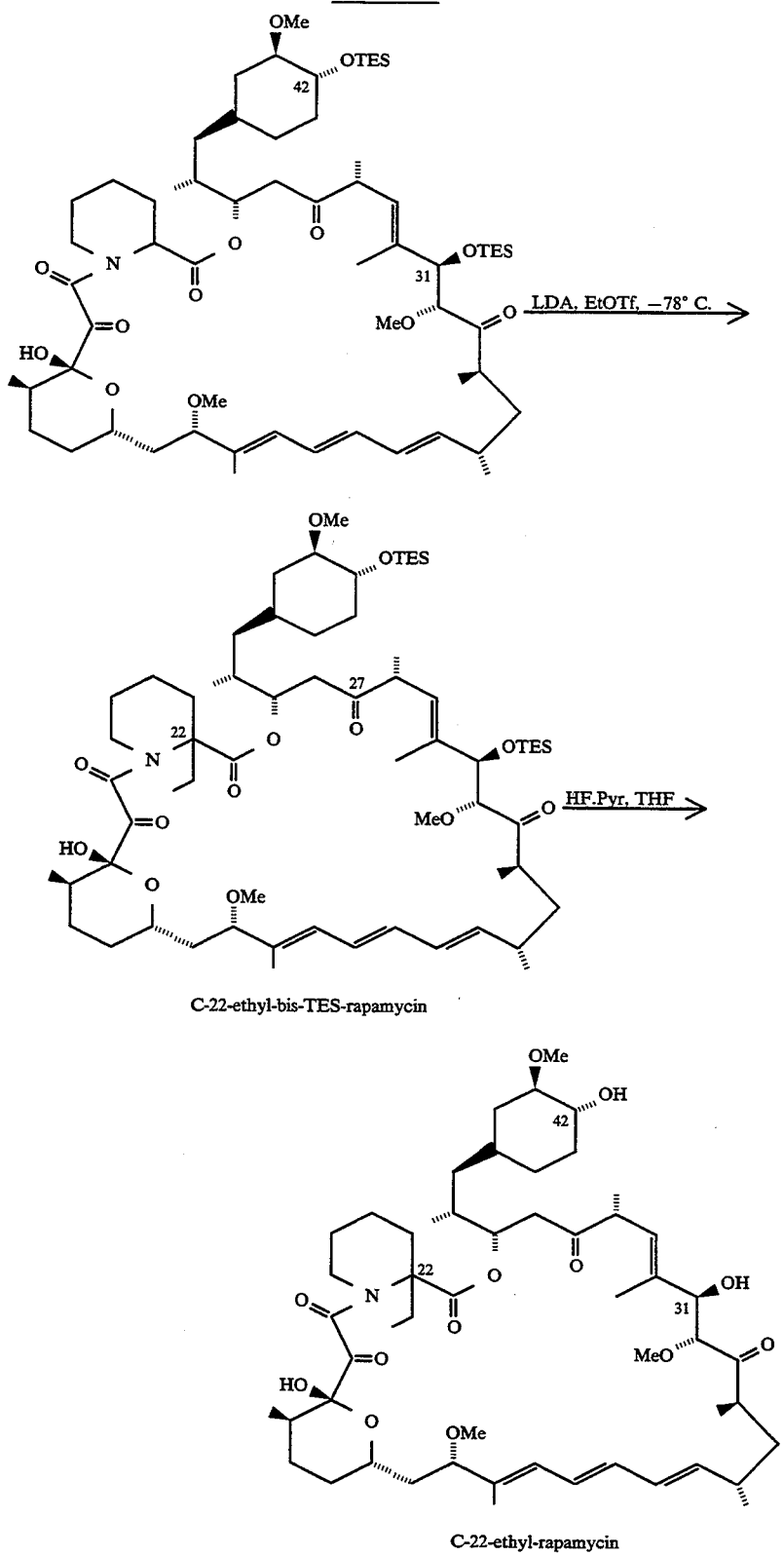

C-22-ethyl-bis-TES-rapamycin

C-22-ethyl-rapamycin

One skilled in the art should understand that derivatives of the present compounds can be easily prepared. For example, one skilled in the art can prepare C-42-acylated derivatives, such as C-42-glycine-C-22-methyl-rapamycin. The C-27 and C-31 positions can be similarly functionalized. In addition, since the proline analogue of rapamycin is known, it is possible to prepare the corresponding alkylated proline analogue, as illustrated in Scheme 3, below:

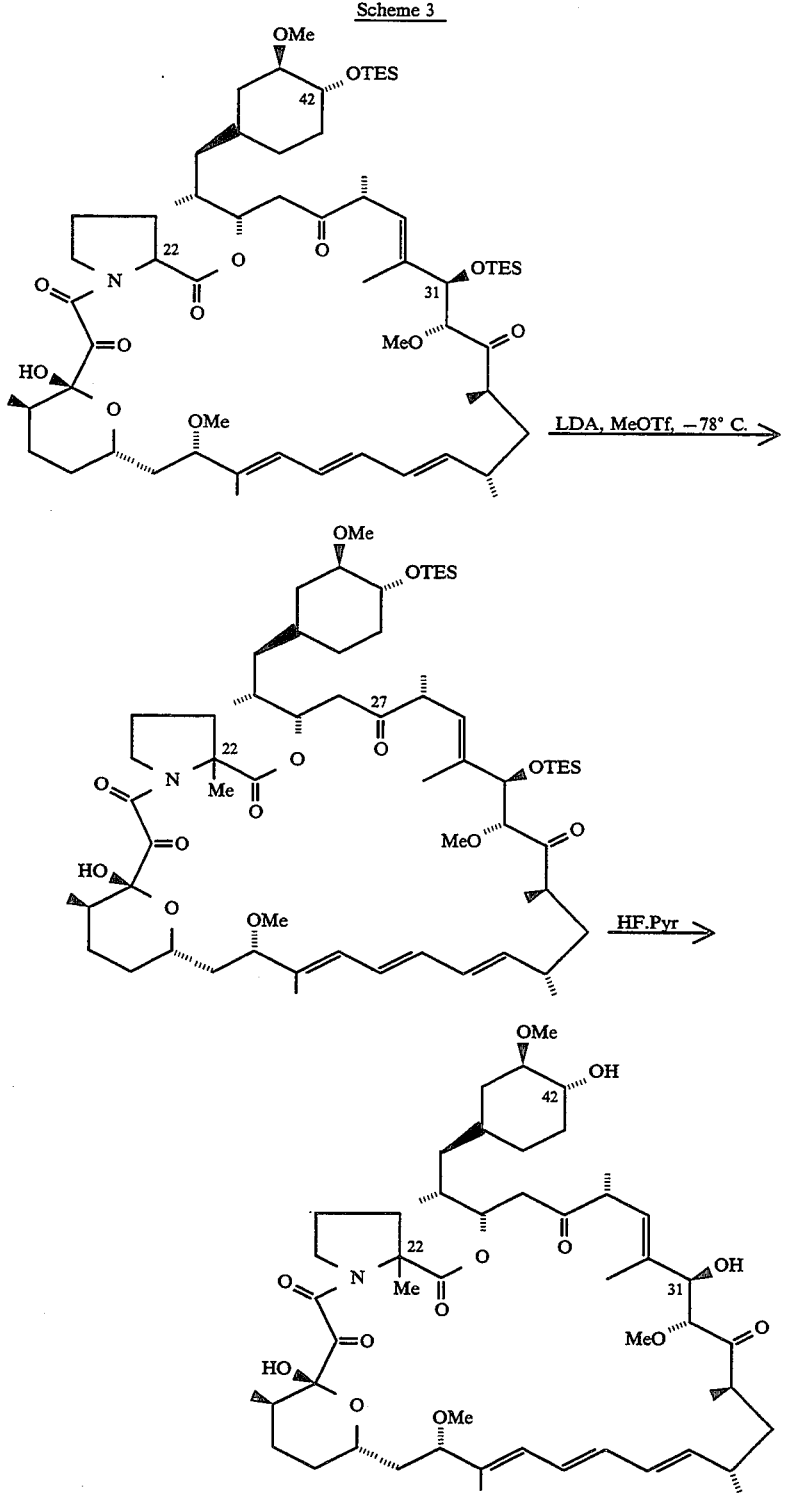

Scheme 3 wherein the substituted methyl group illustrates the desired alkyl group. The C-42 and C-31 functionalized derivatives of the C-22 alkylated proline analogue can also be prepared. Similarly, as in the process depicted in Scheme 1, the C-27 reduced proline analogue can be prepared. This position can also be functionalized as described.

One skilled in the art will readily understand that alkylations at the C-22 position can be carried out via processes well documented in the literature. Such alkylations would include processes utilizing aldehydes of the type:

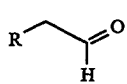

or acid chlorides of the type:

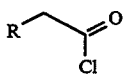

or alkyl halides of the type:

wherein X indicates chlorine, bromine, or iodine. In each of the aldehyde, acid chloride, and alkyl halide formulas, R is intended to indicate a portion of the C-22 substituted $R^1$ substituent indicated above.

It will also be understood that alkylations at the C-22 position can also be carried out utilizing sulfonyl chloride, RSCl, such as where R=lower alkyl or Phenyl, or tosyl cyanide (TsCN). It will be further understood that the thioalkylations contemplated can be accomplished by similar methods. An example would be the protection of hydroxyl groups with TES, treatment with LDA and thioalkylation with dimethyldisulfide or phenyl-s-bromide.

The immunosuppressive activities for representative compounds of this invention were evaluated in an in vitro standard pharmacological test procedure to measure lymphocyte proliferation (LAF) and in an in vivo standard pharmacological test procedure which evaluated the survival time of pinch skin grafts. The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. The results are expressed as an $IC_{50}$.

Representative compounds of this invention were also evaluated in an in vivo test procedure designed to determine the survival time of pinch skin graft from male DBA/2 donors transplanted to male BALB/c recipients. The method is adapted from Billingham R. E. and Medawar P. B., J. Exp. Biol. 28:385–402, (1951). Briefly, a pinch skin graft from the donor is grafted on the dorsum of the recipient as a homograft, and an autograft is used as control in the same region. The recipients are treated with either varying concentrations of cyclosporin A as test control or the test compounds, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

In addition, the stability of representative compounds was tested, via HPLC, in 0.1M phosphate buffer (pH 7.4, 37° C.).

The results of each of these LAF, Skin Graft and Stability tests are provided in the following table:

| Compound | LAF (nM) $IC_{50}$ | Skin Graft (days) (4 mg/kg) | Stability (hours) pH 7.4 buffer |
|---|---|---|---|
| rapamycin | 0.4–9.4 | 12.01 +/− 0.26 | 12–13 |
| 22-methyl-rapamycin | 23.5 | 9.33 +/− 0.52 | 38 |
|  |  | 9.00 +/− 0.63 |  |
|  |  | 10.17 +/− 0.55* |  |
| 22-methyl-27-hydroxyrapamycin | 9.9 | nt | 21.8 |
| 22-ethyl-rapamycin | 140.0 | nt | nt |
| C-22-methyl-42-dimethylglycine-rapamycin | 19.95 | nt | 13.5 |

*tested at 16 mg/kg
nt = not tested

The results of these standard pharmacological test procedures illustrate both in vivo and in vitro immunosuppressive activity for the compounds of the present invention. The results of the LAF test procedure indicate the stabilized rapamycin derivatives induce suppression of T-cell proliferation. As transplanted pinch skin grafts are typically rejected within 6–7 days without the use of an immunosuppressive agent, the increased survival time demonstrated by the use of 22-methyl rapamycin further demonstrates the present invention's utility of immunosuppression.

Because the compounds of this invention are structurally similar to rapamycin and have a similar activity profile to rapamycin, they also are considered to have antitumor, antifungal and antiproliferative activities. As such, the compounds of this invention are useful in the treatment of transplantation rejection, such as heart, kidney, liver, bone marrow and skin transplants; autoimmune diseases such as lupus, rheumatoid arthritis, diabetes mellitus, myasthenia gravis and multiple sclerosis; diseases of inflammation such as psoriasis, dermatitis, eczema, seborrhea, inflammatory bowel disease and eye uveitis; solid tumors; fungal infections; and hyperproliferative vascular diseases, such as restenosis. The present invention, therefore, also provides a method of inducing immunosuppression in a mammal in such need comprising administering to said mammal an immunosuppressive amount of one or more of the compounds discussed herein.

The results of the 0.1M phosphate buffer stability test indicate that the compounds of the present invention have an increased stability relative to rapamycin. As shown above, 22-methyl-rapamycin and 22-methyl-27-hydroxy-rapamycin, respectively, were found to have half lives of 38 and 21.8 hours. These results can be compared to the 12–13 hour half-life determined for rapamycin under the same conditions.

The compounds of this invention can be formulated and provided neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid. carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally, such as in the form of a conventional suppository or ointment.

For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is nontoxic to the skin, and allows delivery of the agent for systemic absorption into the blood stream via the skin. The carrier may take any number of forms, such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1-5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures for other rapamycin compounds, projected daily intravenous dosages of the compounds of this invention would be 0.001-25 mg/kg, preferably between 0.005-5 mg/kg, and more preferably between 0.01-0.5 mg/kg. Projected daily oral dosages of the compounds of this invention would be 0.005-75 mg/kg, preferably between 0.01-50 mg/kg, and more preferably between 0.05-10 mg/kg.

Treatment will generally be initiated with small dosages less than the optimum dose of the compound. Thereafter the dosage is increased until the optimum effect under the circumstances is reached; precise dosages for oral, parenteral, intranasal, intrabronchial, transdermal, or rectal administration will be determined by the administering physician based on experience with the individual subject treated. In general, the compounds of this invention, are most desirably administered at a concentration that will generally afford effective results without causing any harmful or deleterious side effects.

It is contemplated that when the compounds of this invention are used as an immunosuppressive or antiinflammatory agent, they can be administered in conjunction with one or more other immunoregulatory agents. Such other antirejection chemotherapeutic agents include, but are not limited to azathioprine, corticosteroids, such as prednisone and methylprednisolone, cyclophosphamide, rapamycin, cyclosporin A, FK-506, OKT-3, and ATG. By combining one or more of the drugs of the present invention with such other drugs or agents for inducing immunosuppression or treating inflammatory conditions, lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23:507 (1991)].

The following synthesis procedures are provided to demonstrate production methods useful in the preparation of compounds of this invention. These examples and merely illustrative in nature and are not limiting to the scope of this invention.

EXAMPLE 1

C-22-methyl-bis-Tes-rapamycin

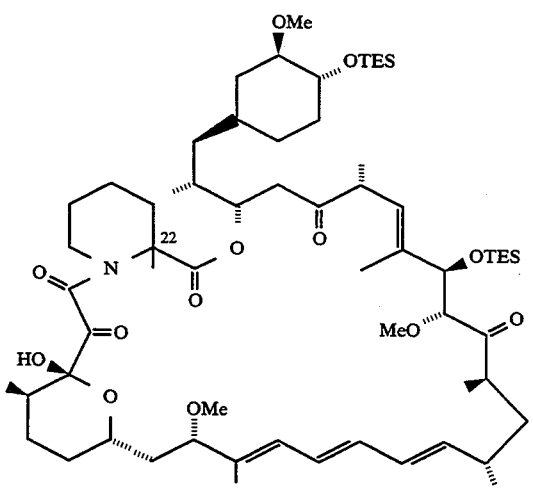

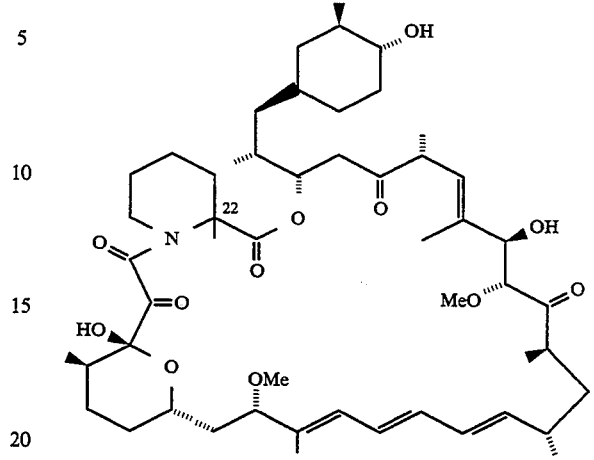

Bis-TES Rapamycin (0.50 g, 0.483 mmol) was dissolved in THF (4.4 mL, 0.1M) and cooled to −78° C. The solution was stirred for 10 min. LDA.THF complex (1.5M in cyclohexane, 0.73 mL, 1.1 mmol) was added dropwise to the solution and stirred for 45 min. Methyl trifluoromethanesulfonate (0.18 g, 1.1 mmol) was added to the reaction and stirred for 1.5 h at −78° C. The reaction was quenched at −78° C. with NaHCO$_3$ (5 mL). The reaction was then allowed to warm to room temperature. The mixture was extracted with ethyl acetate, washed with brine, dried over Na$_2$SO$_4$, and concentrated in vacuo to give a yellow foam. The residue was chromatographed using hexane-ethyl acetate (9:1 then 4:1) as eluant to provide 22-methylated Bil-Tes rapamycin (0.138 g, 27% yield) as a white foam. $^1$H NMR (400 MHz, CDCl$_3$) δ0.50 (comp m, 9H), 0.71 (m, 1H), 0.82–1.59 (comp m, 38H), 1.65 (s, 3H), 1.69 (s, 3H), 1.78 (m, 2H), 1.81 (s, 3H), 1.85–1.95 (comp m, 4H) 205 (m, 2H), 2.32 (m, 3H), 2.36 (s, 1H), 2.39 (s, 1H), 2.61 (m, 2H), 2.89 (m, 1H, 3.14 (s, superimposed on m, 1H), 3.14 (m, 1H), 3.28 (s, 3H), 3.38 (m, 1H), 3.40 (s, superimposed on m, 3H), 3.40 (m, 2H), 3.51 (m, 1H), 3.53 (m, 1H), 3.67 (dd, J=5.71, 9.47 Hz, 1H), 3.79 (d, J=5.57 Hz, 1H), 3.82 (m, 1H), 4.17 (d, J=5.35 Hz, 1H), 4.84 (m, 1H), 5.15 (d, J=10.2 Hz, 1H), 5.42 (dd, J=9.01, 14.2 Hz, 1H), 16.08 (d, J=10.9 Hz, 1H), 6.20 (m, 1H), 6.23 (m, 1H), 6.42 (dd, J=11.01, 14.01 Hz, 1H); high resolution mass spectrum (negative ion FAB) m/z 1155.7 [(M-H)); calcd for C$_{64}$H$_{108}$NO$_{13}$Si$_2$: 1155.7].

EXAMPLE 2

C-22-methyl-rapamycin

C-22-methyl-bis-TES-rapamycin (0.489 g, 0.42 mmol) was dissolved in THF (4 mL) and transferred to a nalgene test tube containing a few 4 Å molecular sieves. In a separate nalgene tube HF/pyridine complex (1 mL) was added to dry pyridine (1 mL) at 0° C. To the substrate at 0° C., 1.8 mL of the aforementioned solution was added. The reaction was held at 0° C. for 15 min. then allowed to warm to room temperature and stir for 2 h. The reaction was then cooled to 0° C. and slowly quenched with NaHCO$_3$. The mixture was extracted with EtOAc, then washed with 0.1N HCl, NaHCO$_3$, and brine. The organic phase was dried over Na$_2$SO$_4$ and evaporated in vacuo. The mixture was chromatographed using 2.5% then 5% MeOH/CH$_2$Cl$_2$ as eluant to yield C-22-methyl-rapamycin (0.36 g, 93% yield). IR (KBr) 3440 (s), 2940 (s), 1725 (s), 1650 (m), 1455 (w), 1380 (w), 1240 (w), 1195 (w), 1090 (s), 995 (m), 915 (w), 735 (w); $^1$H NMR (400 MHz, CDCl$_3$) δ0.67 (m, 1H), 0.90 (d, J=6.38 Hz, 3H), 0.92 (d, J=6.32 Hz, 3H), 1.01 (d, J=6.56 Hz, 3H), 1.05 d, J=7.24 Hz, 3H), 1.07 (d, J=6.95 Hz, 3H), 1.11–1.48 (comp m, 15H), 1.63 (s, 3H), 1.65 (s, 3H), 1.75 (s, 3H), 1.58–2.06 (comp m, 10H), 2.63 (s, 1H), 2.65 (m, 3H), 3.00 (m, 2H), 3.14 (s, 3H), 3.34 (m, 1H), 3.36 (s, 3H), 3.38 (s, 3H), 3.50 (m, 2H), 3.63 (m, 1H), 3.76 (m, 3H), 4.21 (d, J=4.47 Hz, 1H), 4.52 (s, 1H), 5.04 (m, 1H), 5,43 (m, 2H), 6.05 (d, J=10.1 Hz, 1H), 6.13 (m, 1H), 6.25 (m, 1H), 6.41 (m, 1H); high resolution mass spectrum (negative ion FAB) m/z 927 [(M-H); calcd for C$_{52}$H$_{80}$NO$_{13}$: 927].

EXAMPLE 3

C-22-methyl-C-27-hydroxy-bis-TES-rapamycin

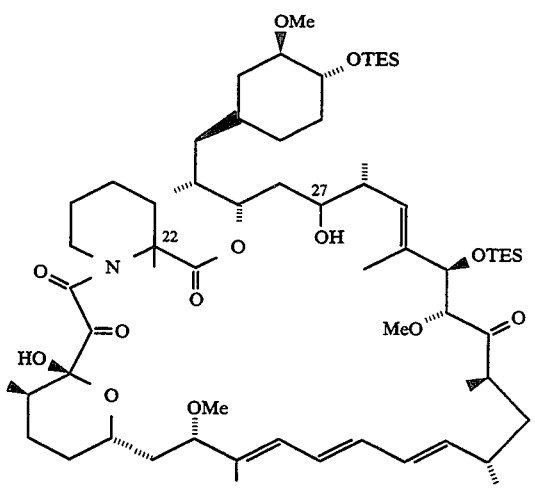
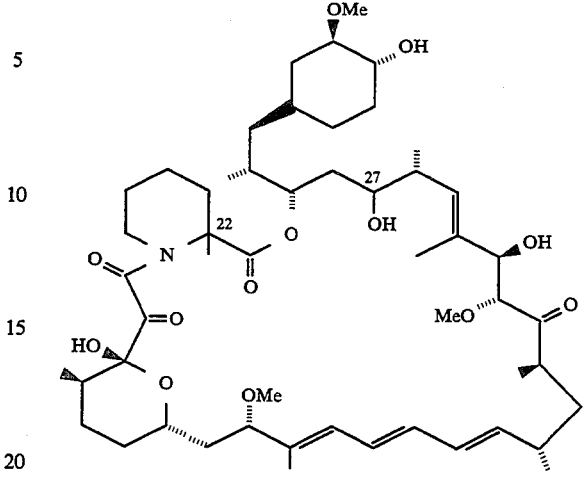

C-22-methyl-bis-TES-rapamycin (0.27 g, 0.23 mmol) was dissolved in THF (1.5 mL) and cooled to −78° C. L-Selectride (1.0M in THF, 0.17 mL) was added rapidly. The reaction was stirred 30 min. then an additional 0.5 equivalents of L-Selectride (0.05 mL) was added. The reaction was warmed slowly to room temperature over 2 h. The mixture was quenched with H$_2$O, extracted with EtOAc, washed with brine, dried over Na$_2$SO$_4$, and evaporated in vacuo. The mixture was chromatographed using 20% then 40% EtOAc/hexane al eluant. The material was further purified by HPLC, 20% EtOAc, Hex, 21 mm silica column to yield Co22-methyl-C-27-hydroxy-bis-TES-rapamycin (0.08 g, 30% yield). $^1$H NMR (400 MHz, CDCl$_3$) δ0.0–0.3 (comp m, 18H), 0.40 (m, 1H), 0.89–0.94 (comp m, 36H), 1.55 (s, 3H), 1.62 (s, 3H), 1.10–2.10 (comp m, 13H), 1.93–2.02 (comp m, 6H), 2.65 (m, 3H), 2.88 (m, 1H), 3.12 (s, 3H), 3.24 (m, 1H), 3.26 (s, superimposed on m, 3H), 3.26 (m, 1H), 340 (s, superimposed on m, 3H), 340 (m, 1H), 3.51 (m, 1H), 3.53 (m, 2H), 3.63 (app.t, J=7.16 Hz, 1H), 3.77 (d, J=5.19 Hz, 1H), 4.17 (d, J=0.62 Hz, 1H), 4.82 (m, 2H), 5.37 (m, 1H), 5.48 9m, 1H), 5.98 (app.t, J=0.62 Hz, 1H), 6.15 (m, 2H), 6.38 (m, 1H); high resolution mass spectrum (negative ion FAB) m/z 1157 [(M-H); calcd for C$_{64}$H$_{110}$NO$_{13}$S$_2$: 1157].

EXAMPLE 4

C-22-methyl-C-27-hydroxy-rapamycin

Reduced methylated Bis-TES Rapamycin (0.055 g, 0.047 mmol) was dissolved in THF (0.5 mL) and transferred to a nalgene test tube containing a few 4 Å molecular sieves. In a separate nalgene tube HF/pyridine complex (1 mL) was added to dry pyridine (1 mL) at 0° C. To the substrate at 0° C., 1.0 mL of the aforementioned solution was added. The reaction was stirred for 15 min. at 0° C. then allowed to stir at room temperature for 2 h. The reaction was then cooled to 0° C. and slowly quenched with NaHCO$_3$. The mixture was extracted with EtOAc, washed with 0.1N HCl, NaHCO$_3$, and brine. The organic phase was dried over Na$_2$SO$_4$ and evaporated in vacuo. The mixture was chromatographed on flash silica gel and was eluted with 2.5% then 5% MeOH/CH$_2$Cl$_2$ to yield C-22-methyl-C-27-hydroxyrapamycin (0.016 g, 36% yield). IR (KBr) 3440 (s), 2920 (s), 1720 (s), 1645 (m), 1455 (m), 1375 (w), 1235 (w), 1190 (w), 1085 (s), 995 (m), 915 (w0, 735(w); $^1$H NMR (400 MHz, CDCl$_3$) δ0.77 (m, 1H), 0.87 (d, J=6.64 Hz, 3H), 0.90 (d, J=6.85 Hz, 3H), 0.93 (d, J=6.64 Hz, 3H), 0.97 (d, J=6.64 Hz, 3H), 1.02 (d, J=6.423 Hz, 3H), 1.04 (m, 1H), 1.18–1.42 (comp m, 15H), 1.61 (s, 3H), 1.63 (s, 3H), 1.65 (s, 3H), 1.53–2.06 (comp m, 10H), 2.28 (m, 2H), 2.65 (m, 2H), 2.92 (m, 2H), 3.10 (m, 1H), 3.13 (s, 3H), 3.32 (s, 3H), 3.36 (m, 2H), 3.38 (s, 3H), 3.51 (m, 2H), 3.61 (app.t, J=7.37 Hz, 1H), 3.78 (d, J=5.19 hz, 1H), 3.87 (m, 1H), 4.29 (m, 1H), 4.30 (s, 1H), 4.81 (m, 1H), 5.40 (m, 2H), 6.00 (d J=10.2, 1H), 6.09 9m, 1H), 6.22 (dd, J=10.4, 14.7 Hz, 1H), 6.37 (dd, J=11.0, 14.73 Hz, 1H); high resolution mass spectrum (negative ion FAB) m/z 929 [(M-H); calcd for C$_{52}$H$_{82}$NO$_{13}$: 929].

EXAMPLE 5

C-22-ethyl-bis-TES-rapamycin

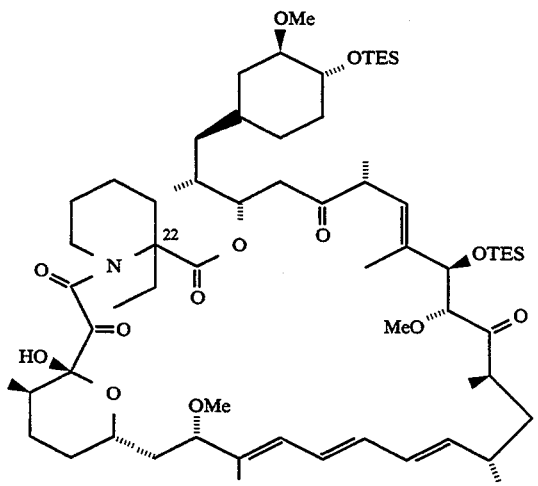
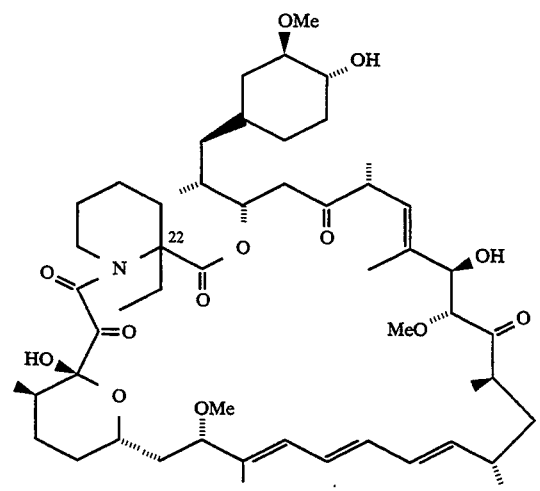

Bis-TES-rapamycin (2.0 g, 1.75 mmol) was dissolved in THF (17.6 mL) and cooled to −78° C. LDA.THF complex (1.5M in cyclohexane, 2.9 mL, 4.38 mmol) was added dropwise to the solution and stirred for 45 min. Ethyl trifluoromethanesulfonate (0.78 g, 4.38 mmol) was added to the reaction and stirred for 2 h at −78° C. The reaction was quenched at −78° C. with a saturated NaHCO$_3$ (5 mL) and allowed to warm to room temperature. The mixture was extracted with ethyl acetate, washed with brine, dried over Na$_2$SO$_4$ and evaporated in vacuo to give a yellow foam. The mixture was chromatographed using 10% then 20% ethyl acetate/hexane as eluant. The material was further purified by HPLC, 20% EtOAc/Hex, on a 41 mm Silica column to yield C-22-ethyl-bis-TES-rapamycin (0.25 g, 13% yield). $^1$H NMR (400 MHz, CDCl$_3$) δ0.0–0.64 (comp m, 18H), 0.73 (m, 1H), 0.85–1.50 (comp m, 46H), 1.54–1.78 (comp m, 3H), 1.67 (s, 3H), 1.80 (s, 3H), 1.85–2.05 (comp m, 4H), 2.32 (m, 3H), 2.37 (s, 1H), 2.41 (s, 1H), 2.56 (m, 2H), 2.89 (m, 1H), 3.14 (m, 1H), 3.15 (s, 3H), 3.26 (s, 3H), 3.40 (s, 3H), 3.42 (m, 1H), 3.48 (s, 1H), 3.50 (s, 1H), 3.74 (m, 1H), 3.89 (m, 1H), 4.14 (m, 1H), 4.88 (m, 2H), 5.16 (d, J=10.3 Hz, 1H), 5.40 (dd, J=9.28, 14.21 Hz, 1H), 6.05 (d, J=11.1 Hz, 1H), 6.16 (m, 1H), 6.25 (m, 1H), 6.43 (dd, J=11.1, 13.9 Hz, 1H); $^{13}$C NMR (100 MHz, CDCl$_3$) δ3.74, 4.37, 4.50, 4.76, 6.31, 6.42, 6.50, 8.33, 9.98, 12.79, 13.18, 13.83, 14.80, 15.25, 15.49, 16.39, 20.71, 21.81, 26.26, 26.71, 29.83, 30.61, 31.31, 31.37, 33.00, 33.94, 34.64, 35.99, 39.23, 39.47, 39.75, 41.34, 41.75, 42.52, 46.06, 48.37, 49.22, 55.56, 56.41, 57.78, 60.40, 64.02, 66.76, 73.62, 75.53, 75.56, 78.85, 83.37, 83.99, 84.16, 85.60, 98.77, 126.54, 126.94, 128.63, 130.87, 132.61, 136.50, 137.14, 139.55, 167.70, 171.56, 172.01, 207.99, 211.38; high resolution mass spectrum (negative ion FAB) m/z 1169.7 [(M-H); calcd for C$_{65}$H$_{111}$NO$_{13}$Si$_2$: 1169.7].

EXAMPLE 6

C-22-ethyl-rapamycin

C-22-ethyl-bis-TES-rapamycin (0.25 g, 0.21 mmol) was dissolved in THF (2 mL) and transferred to a nalgene test tube containing a few 4 Å molecular sieves. In a separate nalgene tube HF/pyridine complex (1 mL,) was added to dry pyridine (1 mL) at 0° C. To the substrate at 0° C., 1.8 mL of the aforementioned solution was added. The reaction was stirred for 15 min. at 0° C. then allowed to stir at room temperature for 2 h. The reaction was then cooled to 0° C. and slowly quenched with NaHCO$_3$. The mixture was extracted with EtOAc, washed with 0.1N HCl, NaHCO$_3$, and brine. The organic phase was dried over Na$_2$SO$_4$ and evaporated in vacuo. The mixture was chromatographed using 2.5% then 5% MeOH/CH$_2$Cl$_2$ as eluant to yield C-22-ethyl-rapamycin (0.13 g, 64% yield). IR(KBr) 3440(s), 2940 (s), 1725 (s), 1650 (m), 1460 (w), 1380 (w), 1235 (w), 1190 (w), 1090 (s), 995 (m), 915 (w), 735 (w); $^1$H NMR (400 MHz, CDCl$_3$) δ0.68 (m, 1H), 0.87–1.06 (comp m, 15H), 1.06–1.45 (comp m 15H), 1.57 (m, 3H), 1.66 (s, 3H), 1.75 (s, 3H), 190–2.08 (comp m 10H), 2.31 (m, 3H), 2.64 (m, 3H), 2.89 (s, 1H), 2.90 (m, 2H), 3.13 (s, 3H), 3.33 (m, 1H), 3.38 (s, 3H), 3.47 (m, 2H), 3.66 (app.t, J=7.24 Hz, 1H), 3.82 (d, J=5.47 Hz, 1H), 3.95 (m, 1H), 4.21 (d, J=5.54 Hz, 1H), 4.43 (s, 1H), 5.09 (m, 1H), 5.37 (d, J=9.62 Hz, 1H), 5.42 (d, J=9.49 Hz, 1H), 6.05 (d, J=10.93 Hz, 1H), 6.13 (dd, J=10.5, 14.8 Hz, 1H), 6.24 (m, 1H), 6.39 (m, 1H); $^{13}$C NMR (100 MHz, CDCl3) δ8.53, 10.19, 13.44, 13.98, 15.66, 15.91, 15.96, 16.53, 21.83, 21.97, 26.47, 26.93, 29.74, 30.79, 31.23, 31.44, 32.79, 33.27, 34.10, 34.59, 35.97, 39.12, 39.89, 40.04, 40.66, 41.36, 42.76, 46.20, 55.85, 56.58, 58.94, 64.17, 67.41, 73.97, 74.97, 74.96, 76.81, 83.37, 84.42, 85.16, 98.82, 126.84, 127.03, 128.66, 130.78, 132.82, 135.61, 136.99, 139.66, 167.40, 172.03, 194.05, 207.88, 213.99; high resolution mass spectrum (negative ion FAB) m/z 941 [(M-H); calcd for C$_{53}$H$_{82}$NO$_{13}$: 941].

EXAMPLE 7

Synthesis of C-22-methyl-42-dimethylglycine rapamycin

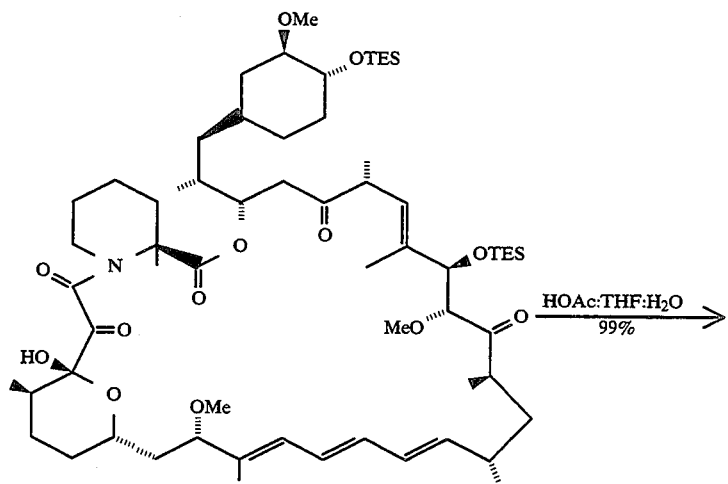
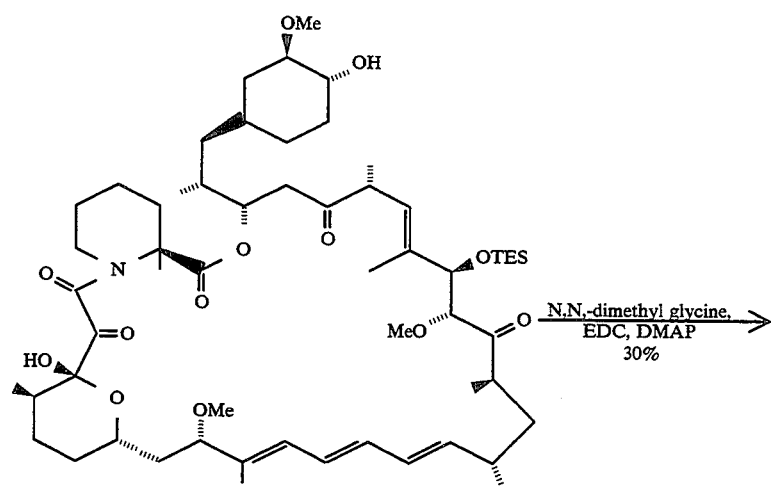
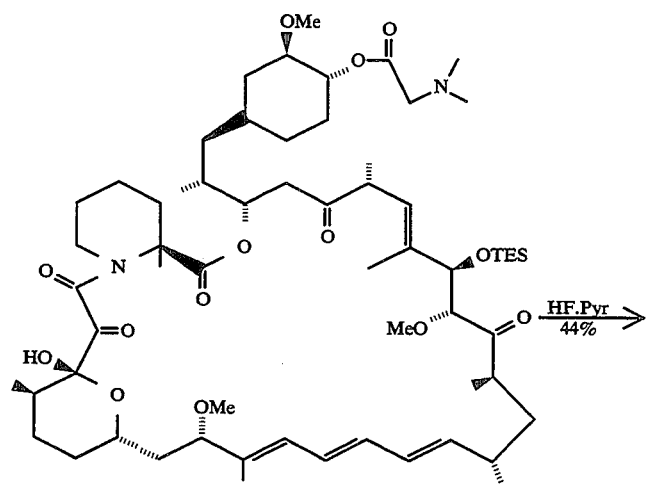

-continued

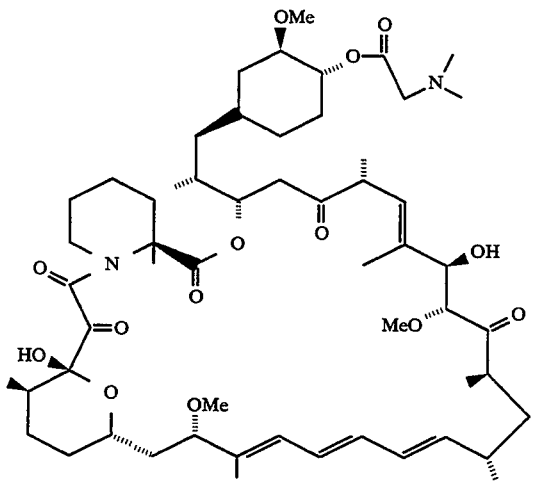

a) Mono-deprotection of 22-Methylated Bis-TES

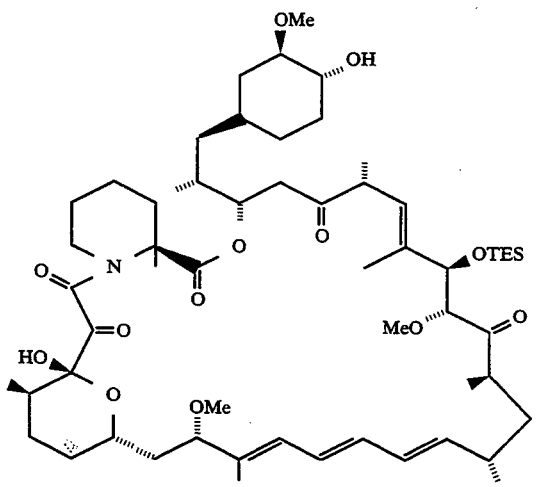

Methylated Bis-TES Rapamycin (0.42 g, 0.36 mmol) was dissolved in a 3:1:1 solution of HOAc:THF:H$_2$O. The reaction was complete by TLC in 10 minutes and was quenched with NaHCO$_3$ and stirred for 10 min. The mixture was extracted with EtOAc, dried over Na$_2$SO$_4$, filtered and evaporated in vacuo. The residue was chromatographed on silica gel eluted with 2.5% MeOH/CH$_2$Cl$_2$ to yield mono-TES methylated rap (0.37 g, 99% yield). $^1$H NMR (300 MHz, CDCl$_3$) δ0.47 (m, 6H), 0.68 (m, 1H), 0.79–1.0 (comp m, 30H), 1.01–1.83 (comp m, 13H), 1.60 (s, 3H), 1.63 (s, 3H), 1.75 (s, 3H), 1.92 (m, 2H), 2.10 (m, 3H), 2.31 (m, 2H), 2.65 (m, 2H), 2.91 (m, 1H), 3.16 (s, 3H), 3.21 (m, 2H), 3.29 (s, 3H), 3.36 (s, 3H), 3.53 (m, 2H), 3.64 (m, 1H), 3.78 (m, 1H), 3.81 (m, 1H), 4.14 (d, 1H), 4.75 (s, 1H), 4.85 (m, 1H), 5.13 (m, 1H), 5.4 (m, 1H), 6.07 (m, 1H), 6.2 (m, 2H), 6.4 (m, 1H).

b) Acylation of 22-methylated mono-TES

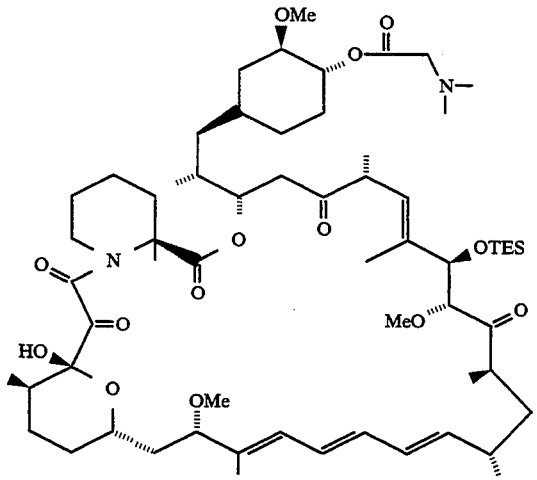

Methylated mono-TES Rapamycin (0.36 g, 0.35 mmol) was dissolved in methylene chloride (8 mL). Dimethylglycine (3 eq., 0.11 g), (3-Dimethylaminopropyl)-3-ethylcarbodiimide hydrochloride (4 eq., 0.27 g), and spatula tip of DMAP were added sequentially to the reaction which was then allowed to stir overnight. The reaction was then diluted with methylene chloride and washed with water. The aqueous phase was extracted with methylene chloride. The combined organics were washed once again with water then dried over Na$_2$SO$_4$, filtered, and evaporated in vacuo. The mixture was chromatographed on silica gel eluted with 1% then 2.5% MeOH/CH$_2$Cl$_2$ to provide 42-glycinate mono-TES rap (0.12 g, 30% yield). $^1$H NMR (400 MHz, CDCl$_3$) δ0.73–1.06 (comp m, 30H), 1.18–1.81 (comp m, 23H), 1.62 (s, 3H), 1.67 (s, 3H), 1.82 (s, 3H), 1.87–2.1 (comp m, 4H), 2.41 (s, 6H), 2.63 (m, 2H), 3.16 (m, 2H), 3.29 (s, 3H), 3.35 (s, 3H), 3.36 (s, 2H), 3.21–3.37 (comp m, 2H), 3.53 (m, 2H), 3.68 (app.t, J=7.41 Hz, 1H), 3.89 (m, 2 H), 4.18 (d, J=4.1 Hz, 1H), 4.74 (m, 1H), 4.80 (s, 1H), 4.92 (m, 1H), 5.20 (d, J=10.4 Hz, 1H), 5.40 (dd, J=7.0, 7.1 Hz, 1H), 6.09 (d, J=10.7 Hz, 1H), 6.22 (m, 2H), 6.42 (dd, J=7.1, 7.2 Hz, 1H); high resolution mass spectrum (negative ion FAB) m/z 1126.5 [(M-.); calcd for C$_{62}$H$_{102}$NO$_{14}$Si: 1126.5].

c) Deprotection of 42-glycinate mono-TES

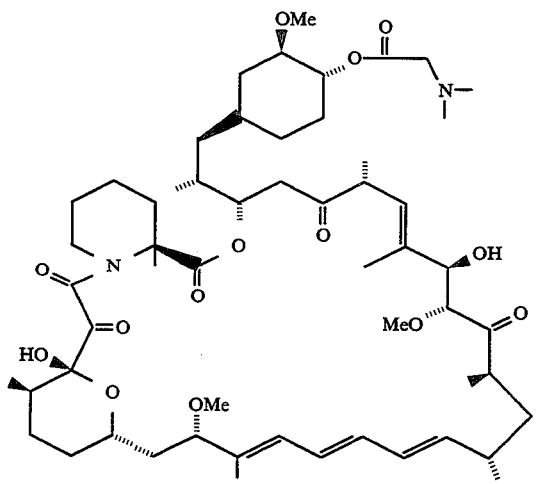

42-glycinate mono-TES Rapamycin (0.11 g, 0.1 mmol) was dissolved in THF (2 mL) and transferred to a nalgene test tube containing a few 4 Å molecular sieves. In a separate nalgene tube 1 ml of HF/pyridine complex was added to 1 ml of dry pyridine at 0° C. 1 ml of this solution was added to the test tube containing the substrate at 0° C. The reaction was stirred for 15 min. then the ice bath was removed and the reaction allowed to stir at room temperature for 2 h. The reaction was then cooled to 0° C. and slowly quenched with NaHCO$_3$. The mixture was extracted with EtOAc, washed with 0.1N HCl, NaHCO$_3$, and brine consecutively. The organic The mixture was extracted with phase was dried over Na$_2$SO$_4$ and evaporated in vacuo. The mixture was chromatographed on silica gel eluted with 2.5% then 5% MeOH/CH$_2$Cl$_2$ to yield C-22-methyl-42-glycinate rap (0.043 g, 44% yield). IR (KBr) 3440 (s), 2940 (s), 1730 (s), 1650 (m), 1460 (m), 1375 (w), 1290 (w), 1240 (w), 1190 (w), 1135 (w), 1100 (m), 990 (w), 730 (w); $^1$H NMR (400 MHz, CDCl$_3$) δ0.84 (dd, J=12.1, 12.2 Hz, 1H), 0.89 (d, J=5.26 Hz, 3H), 0.91 (d, J=5.32 Hz, 3H), 1.00 (d, J=6.56 Hz, 3H), 1.05 (d, J=1.7 Hz, 3H), 1.07 (d, J=1.73 Hz, 3H), 0.87–1.45 (comp m, 15H), 1.46–2.08 (comp m, 10H), 1.61 (s, 3H), 1.65 (s, 3H), 1.75 (s, 3H), 2.35 (s, 6H), 2.65 (m, 2H), 2.95 (s, 1H), 3.14 (s, 3H), 3.15 (m, 1H), 3.17 (s, 2H), 3.32 (m, 1H), 3.34 (s, 3H), 3.36 (s, 3H), 3.37 (m, 1H), 3.50 (m, 2H), 3.64 (app.t, J=7.4 Hz, 1H), 3.79 (m, 2H), 4.22 (d, J=5.7 Hz, 1H), 4.46 (s, 1H), 4.59 (m, 1H), 5.04 (m, 1H), 5.41 (d, J=9.92 Hz, 1H), 5.44 (dd, J=4.2, 7.1 Hz, 1H), 6.05 (d, J=10.4 Hz, 1H), 6.13 (dd, J=10.4, 12.6 Hz, 1H), 6.26 (dd, J=12.6, 12.7 Hz, 1H), 6.38 (dd, J=7.2, 7.3 Hz, 1H); $^{13}$C NMR (100 MHz, CDCl$_3$) δ10.15, 13.31, 14.02, 15.72, 16.01, 16.08, 17.17, 19.67, 21.81, 22.50, 26.96, 29.77, 30.91, 31.10, 32.88, 32.96, 33.71, 33.77, 35.80, 36.28, 38.84, 39.66, 39.98, 40.64, 41.32, 42.44, 45.21, 46.25, 55.93, 57.21, 59.09, 60.85, 67.32, 75.14, 76.33, 76.69, 77.00, 77.21, 77.32, 80.79, 83.68, 85.43, 98.66, 126.85, 128.93, 130.59, 133.03, 135.75, 136.49, 139.94, 167.86, 170.19, 172.36, 194.84, 207.97, 214.39; high resolution mass spectrum (negative ion FAB) m/z 1012.6 [(M-.); calcd for C$_{62}$H$_{102}$NO$_{14}$Si: 1012.6].

What is claimed:
1. A compound of the formula:

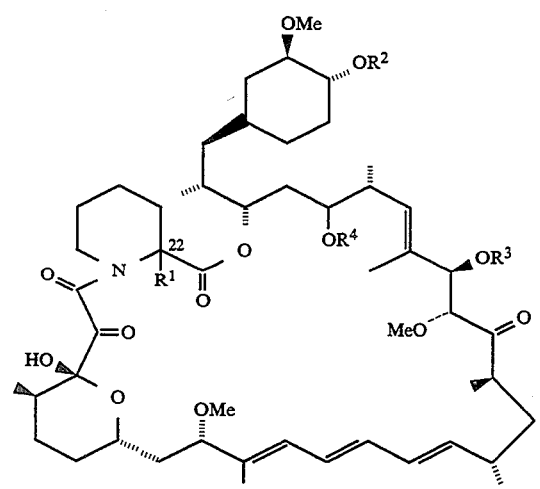

or

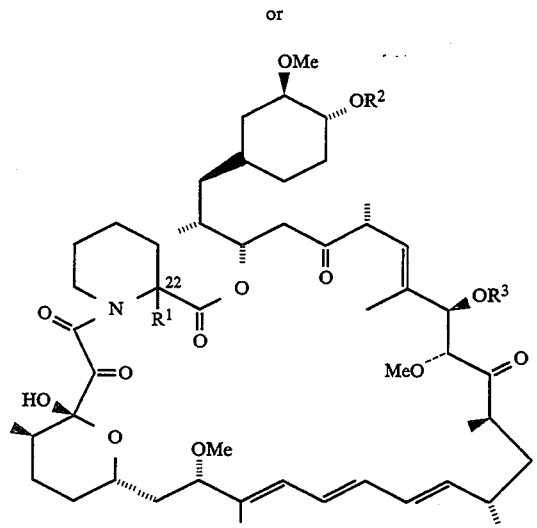

wherein
$R^1$ is C$_1$–C$_6$ lower alkyl, C$_1$–C$_6$ lower acyl, C$_1$–C$_6$ alkylthio, C$_6$–C$_{10}$ aryl, C$_7$–C$_{16}$ arylalkyl, C$_6$–C$_{10}$ arylthio, C$_7$–C$_{16}$ arylalkylthio, cyano, C$_1$–C$_6$ perfluorinated lower alkyl, or

wherein R is a chain of 1–5 carbon atoms; and
$R^2$, $R^3$ and $R^4$ are each independently hydrogen or SiEt$_3$; or a pharmaceutically acceptable salt thereof.

2. A compound of claim 1 which is C-22-methyl-rapamycin or a pharmaceutically acceptable salt thereof.

3. A compound of claim 1 which is C-22-ethyl-rapamycin or a pharmaceutically acceptable salt thereof.

4. A compound of claim 1 which is C-22-methyl-C-27-hydroxy-rapamycin or a pharmaceutically acceptable salt thereof.

5. A compound of claim 1 which is C-22-ethyl-C-27-hydroxy-rapamycin or a pharmaceutically acceptable salt thereof.

6. A compound of the formula:

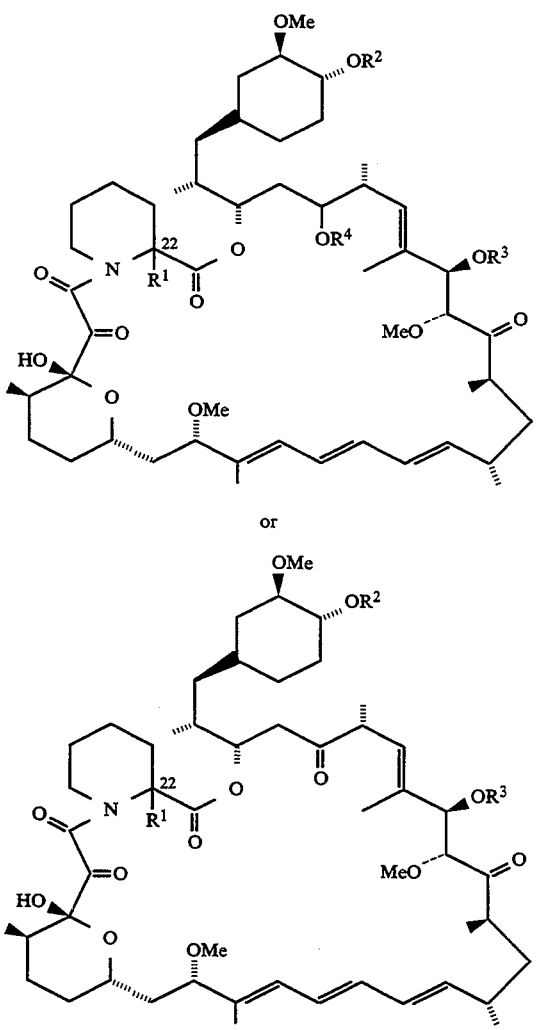

or wherein
R[1] is $C_1-C_6$ lower alkyl, $C_1-C_6$ alkylthio, $C_6-C_{10}$ aryl, $C_7-C_{16}$ arylalkyl, $C_6-C_{10}$ arylthio, $C_7-C_{16}$ arylalkylthio, cyano, $C_1-C_6$ perfluorinated lower alkyl, or

wherein R is a chain of 1–5 carbon atoms; and R[2], R[3], and R[4] are each independently:
a.) hydrogen; or
b.) SiEt$_3$; or

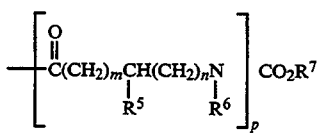

wherein
R[5] is hydrogen, alkyl of 1–6 carbon atoms, aminoalkyl of 1–4 carbon atoms, aralkyl of 7–10 carbon atoms, —(CH$_2$)$_q$CO$_2$R[8], —(CH$_2$)$_r$NR[9]CO$_2$R[10], carbamylalkyl of 2–3 carbon atoms, hydroxyalkyl of 1–4 carbon atoms, guanylalkyl of 2–4 carbon atoms, mercaptoalkyl of 1–4 carbon atoms, alkylthioalkyl of 2–6 carbon atoms, indolylmethyl, hydroxyphenylmethyl, imidazolylmethyl or phenyl which is optionally mono-, di- or tri-substituted with a substituent selected form alkyl of 1–6 carbon atoms, alkoxy of 1–6 carbon atoms, hydroxy, cyano, halo, nitro, carbalkoxy of 2–7 carbon atoms, trifluoromethyl, amino, or —CO$_2$H;

R[6] and R[9] are each, independently, hydrogen, alkyl of 1–6 carbon atoms, or aralkyl of 7–10 carbon atoms;

R[7], R[8], and R[10] are each, independently, alkyl of 1–6 carbon atoms, aralkyl of 7–10 carbon atoms, fluorenylmethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO$_2$H;

m is 0–4;
n is 0–4;
p is 1–2;
q is 0–4;
r is 0–4; wherein
R[5], R[6], m, and n are independent in each of the

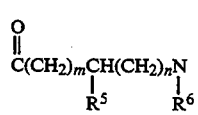

subunits when p=2; or d.) —CONH(CR[11]R[12])$_n$—X wherein

R[11] and R[12] are each, independently, hydrogen, alkyl of 1–6 carbon atoms, aralkyl of 7–10 carbon atoms, cycloalkyl of 3–8 carbon atoms, halogen, or trifluoromethyl;

X is hydrogen, lower alkyl of 1–6 carbon atoms, cycloalkyl of 3–8 carbon atoms, trifluoromethyl, nitro, alkoxy of 1–6 carbon atoms, carboalkoxy of 2–7 carbon atoms, aralkyl of 7–10 carbon atoms, halo, dialkylamino of 1–6 carbon atoms per alkyl group, thioalkyl of 1–6 carbon atoms, or Y;

Y is a phenyl group which may be optionally mono-, di-, or tri-substituted with a group selected from alkyl of 1–6 carbon atoms, aralkyl of 7–10 carbon atoms, alkoxy of 1–6 carbon atoms, cyano, halo, nitro, carbalkoxy of 2–7 carbon atoms, trifluoromethyl, dialkylamino of 1–6 carbon atoms per alkyl group, alkylthio of 1–6 carbon atoms, —SO$_3$H, —PO$_3$H, or —CO$_2$H;

n=0–5; with the proviso that R[2], R[3] and R[4] are not all hydrogen and when n=0, X is lower alkyl of 1–6 carbon atoms, cycloalkyl of 3–8 carbon atoms, aralkyl of 7–10 carbon atoms, or Y; or e.) 

wherein
R[13] is a mono-, di-, poly-, or per-fluorinated alkyl group of 1–10 carbon atoms, with the proviso that R[2], R[3] and R[4] are not all hydrogen, alkyl of 1–10 carbon atoms, arylalkyl of 7–10 carbon atoms, or aryl wherein the aryl group may be optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO$_3$H, —PO$_3$H, and —CO$_2$H; or f.) 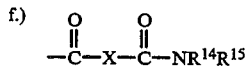

wherein

X is —(CH$_2$)$_m$— or —Ar—;

R$^{14}$ and R$^{15}$ are each, independently, hydrogen, alkyl of 1-12 carbon atoms, —(CH$_2$)$_n$—Ar, —(CH$_2$)$_p$—NR$^{16}$R$^{17}$, or —(CH$_2$)$_p$—N+R$^{16}$R$^{17}$R$^{18}$Y—;

R$^{16}$ and R$^{17}$ are each, independently, hydrogen, alkyl of 1-12 carbon atoms, or —(CH$_2$)$_n$—Ar;

Ar is an optionally mono- or di-substituted group selected from

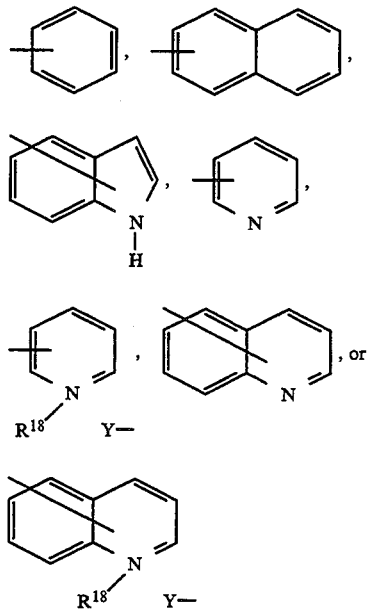

in which the optional substituents are selected from the group consisting of alkyl of 1-6 carbon atoms, aralkyl of 7-10 carbon atoms, alkoxy of 1-6 carbon atoms, cyano, halo, nitro, carbalkoxy of 2-7 carbon atoms, or perfluoroalkyl of 1-6 carbon atoms;

R$^8$ is alkyl of 1-6 carbon atoms;

Y is a halide, sulfate, phosphate, or p-toluenesulfonate anion;

m=1-6;
n=1-6;
p=1-6; or g.) —CONHSO$_2$—Ar wherein

Ar is phenyl, naphthyl, pyridyl, quinolyl, isoquinolyl, quinoxalyl, thienyl, thionaphthyl, furyl, benzofuryl, benzodioxyl, benxoxazolyl, benzoisoxazolyl, or benzodioxolyl; wherein the Ar group may be optionally mono-, di-, or tri-substituted with a group selected from alkyl of 1-6 carbon atoms, arylalkyl of 7-10 carbon atoms, alkoxy of 1-6 carbon atoms, cyano, halo, nitro, carbalkoxy of 2-7 carbon atoms, trifluoromethyl, amino, dialkylamino of 1-6 carbon atoms per alkyl group, alkylthio of 1-6 carbon atoms, —SO$_3$H, —PO$_3$H, or —CO$_2$H; with the proviso that R$^2$, R$^3$ and R$^4$ are not all hydrogen; or a pharmaceutically acceptable salt thereof when the Ar group contains a basic nitrogen or when the Ar group is substituted by dialkylamino of 1-6 carbon atoms per alkyl group, —SO$_3$H, —PO$_3$H, or —CO$_2$H;

h) —SO$_2$R$^{19}$ wherein

R$^{19}$ is alkyl, alkenyl, or alkynyl containing 1 to 6 carbon atoms; or an aromatic moiety selected from the group consisting of phenyl and naphthyl or a heterocyclic moiety selected from the group consisting of thiophenyl and quinolinyl or NHCO$_2$R$^{20}$ wherein R$^{20}$ is lower alkyl containing 1 to 6 carbon atoms; or i) 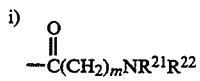

wherein

R$^{21}$ and R$^{22}$ are each, independently, hydrogen or alkyl of 1-3 carbon atoms or, if R$^{21}$ and R$^{22}$ are alkyl of 1-3 carbon atoms, R$^{21}$ and R$^{22}$ together with the nitrogen to which they are attached form a saturated heterocyclic ring having 4-5 carbon atoms; and m=1-3: or j) 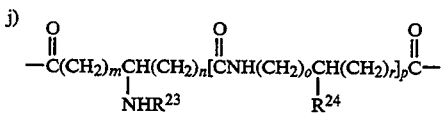

wherein

R$^{24}$ is hydrogen, alkyl of 1-6 carbon atoms, arylalkyl of 7-10 carbon atoms, (CH$_2$)$_s$NR$^{25}$R$^{26}$, aminoalkyl of 1-4 carbon atoms, hydroxyalkyl of 1-4 carbon atoms, guanylalkyl of 2-4 carbon atoms, mercaptoalkyl of 1-4 carbon atoms, alkylthioalkyl of 2-6 carbon atoms, indolmethyl, hydroxyphenylmethyl, imidazolylmethyl, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or —CO$_2$H;

R$^{25}$ is hydrogen, alkyl of 1-6 carbon atoms, or aralkyl of 7-10 carbon atoms;

R$^{23}$ and R$^{26}$ are each independently hydrogen, formyl, alkanoyl of 2-7 carbon atoms, arylalkanoyl of 8-11 carbon atoms, aryloyl, or CO$_2$R$^{27}$;

R$^{27}$ is alkyl of 1-6 carbon atoms, arylalkyl of 7-10 carbon atoms, allyl, fluorenylmethyl, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino or —CO$_2$H;

m is 0-4;
n is 0-4;
p is 0-1;
q is 0-4;
r is 0-4; and
s is 0-4 or a pharmaceutically acceptable salt thereof.

7. A compound of claim 6 which is C-22-methyl-42-dimethylglycine rapamycin.

* * * * *